United States Patent [19]

Metz

[11] Patent Number: 5,312,382

[45] Date of Patent: May 17, 1994

[54] TWO-PIECE OSTOMY APPLIANCE WITH FACEPLATE BISTABLE COUPLING RING

[75] Inventor: Michael Metz, Chicago, Ill.

[73] Assignee: Hollister Incorporated, Libertyville, Ill.

[21] Appl. No.: 70,894

[22] Filed: Jun. 3, 1993

[51] Int. Cl.⁵ ............................................. A61F 5/44
[52] U.S. Cl. ................................. 604/338; 604/332; 604/342
[58] Field of Search ................ 604/277, 278, 332–345

[56] References Cited

U.S. PATENT DOCUMENTS

| | | | |
|---|---|---|---|
| 4,419,100 | 12/1983 | Alexander | 604/339 |
| 4,610,676 | 9/1986 | Schneider et al. | 604/339 |
| 4,610,677 | 9/1986 | Mohiuddin | 604/339 |
| 4,772,279 | 9/1988 | Brooks et al. | 604/339 |
| 4,868,024 | 9/1989 | Cross et al. | 604/332 |
| 4,917,689 | 4/1990 | Coombes | 604/338 |
| 4,973,323 | 11/1990 | Kaczmarek et al. | 604/332 |
| 5,167,651 | 12/1992 | Leise, Jr. et al. | 604/339 |

*Primary Examiner*—Randall L. Green
*Assistant Examiner*—Rob Clarke
*Attorney, Agent, or Firm*—Tilton Fallon Lungmus

[57] ABSTRACT

A two-piece ostomy appliance comprising a pouch component and a faceplate component. The faceplate component has disposed thereon a dual-state, bistable coupling ring with a latching member for sealingly engaging the periphery of an opening in the pouch component. The coupling ring has an annular base defining a central opening and a contact face thereon surrounding the central opening. An annular collar extends from the base and a bistable latching member is joined to the collar along an annular hinge line, the latching member providing a contact surface and being pivotable about said hinge line. The latching member pivots about the hinge line between a stable, substantially untensioned first state wherein the latching member projects generally axially away from the collar and a stable, tensioned second state wherein the latching member extends in a reverse direction towards the annular base with said contact face of the latching member being positioned for tight engagement with the annular base's contact face or with the annular periphery of the pouch component clamped between the base and the latching member.

12 Claims, 1 Drawing Sheet

TWO-PIECE OSTOMY APPLIANCE WITH FACEPLATE BISTABLE COUPLING RING

BACKGROUND AND SUMMARY

Current two-piece ostomy couplings generally require axial compressive forces to secure a pouch ring onto a faceplate ring. Typically, an element of the pouch ring stretches or deforms as it is applied over the faceplate ring bringing such surfaces into leakproof contact. For a more detailed description of such two-piece ostomy appliances, reference may be had to coowned U.S. Pat. Nos. 4,610,676, 4,610,677 and 4,419,100.

Recent interest has been shown in providing "flushable" ostomy appliances which are formed of materials, or combinations of materials, capable of dissolving or dispersing when the appliance is discarded into a flush toilet or water closet. Reference may be had to U.S. Pat. Nos. 4,772,279, 4,868,024 and 4,917,689 as illustrative of such flushable ostomy appliances. While the pouches of conventional two-piece systems might seem appropriate candidates for flushable construction, a major disadvantage is that the pouch coupling rings of such two-piece appliances are commonly formed of tough, durable, and semi-rigid polymers such as polyethylene which are incapable of dissolving or dispersing in water and would therefore present a risk of clogging and possibly damaging toilets and sewer systems. Another disadvantage encountered when using a flushable pouch with a two-piece appliance is that a flushable pouch usually has at least one water soluble layer which may have edges exposed to fluids passing through the pouch's stoma-receiving opening and such exposure may result in premature structural failure of the pouch component.

The present invention addresses these problems by providing a bistable coupling ring which has a latching member on the faceplate component such that the latching member releasably engages the edge portion of the pouch's stoma-receiving opening. Since the bistable coupling ring of the faceplate directly engages the film of the pouch about the stoma-receiving opening, the pouch component does not require a semi-rigid ring or flange which could prevent the pouch from being easily disposable in a toilet bowl or water closet. Furthermore, the bistable coupling ring of the present invention provides a fluid tight seal and latching interconnection with the pouch, thereby protecting exterior water soluble layers of the pouch from contact with body fluids which may flow through the pouch's stoma-receiving opening.

The present invention provides a faceplate for a two-piece collection system comprising a thin, flexible adhesive pad for adhesive attachment to a skin surface, a coupling ring formed of flexible, semi-rigid polymeric material, and attachment means for joining the coupling ring to the flexible pad. The coupling ring has an annular base defining a central opening and a contact face thereon surrounding said opening. An annular collar extends from the base adjacent to and concentric with said opening. A bistable annular latching member is joined to the collar along an annular hinge line, said latching member providing a contact surface and being pivotable about the hinge line between a stable, substantially untensioned first state wherein the latching member projects generally axially away from the collar and a stable, tensioned second state wherein the latching member extends reversely towards the base with the contact surface of said latching member positioned for tight engagement with the base's contact face. When the latching member is in its first state, the coupling ring may be inserted into the opening of the pouch component and, thereafter, the latching member can be shifted to its second state so that the pouch component is clamped between the contact surface of the latching member and the contact face of the base. In such second state, the latching member forcefully engages the interior of the pouch component so as to produce a fluid-tight interlock between the parts. Therefore, the pouch component does not require a coupling ring or flange which could interfere with effective disposal of the pouch, and the coupling ring engages the interior of the pouch component so as to shield the exterior layers of the pouch component which may be water soluble.

Other features, advantages, and objects will become apparent from the specification and drawings.

DRAWINGS

DETAILED DESCRIPTION OF PREFERRED EMBODIMENT

Figure 1:
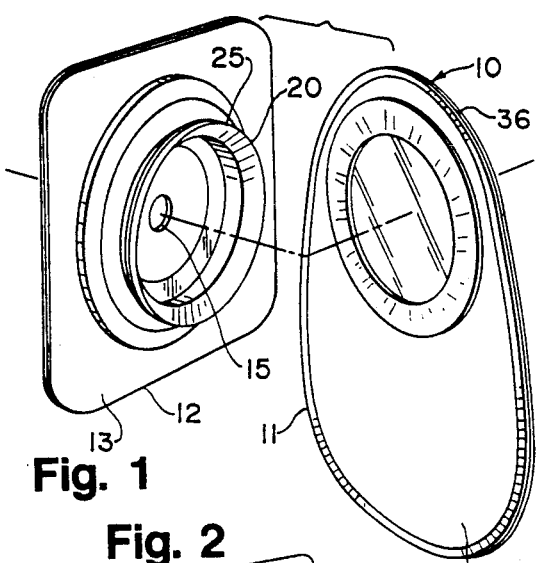
FIG. 1 is a perspective view of a two-piece ostomy appliance embodying this invention, the appliance being shown with the pouch component uncoupled from the faceplate component for clarity of illustration.

In FIG. 1, the numeral 10 generally designates a two-piece ostomy appliance comprising a pouch component 11 and a faceplate component 12. Except as described below, the faceplate component 12 may be of known construction and, in the embodiment illustrated, comprises a flexible panel 13 composed of an inner ring 13a of thermoplastic film and an outer patch or ring 13b of microporous material or other suitable sheet material. The microporous patch 13b is provided with a coating of pressure sensitive adhesive 14 along one surface for peristomal attachment to a patient. The film ring 13a may be backed by a layer 13c of soft, pliant, moisture-absorbing adhesive material commonly known in the medical field as protective skin barrier material. The faceplate component 12 has a stoma-receiving opening 15 which may be reformed or enlarged by cutting prior to application so as to conform generally with the size and shape of the patient's stoma.

Figure 2:
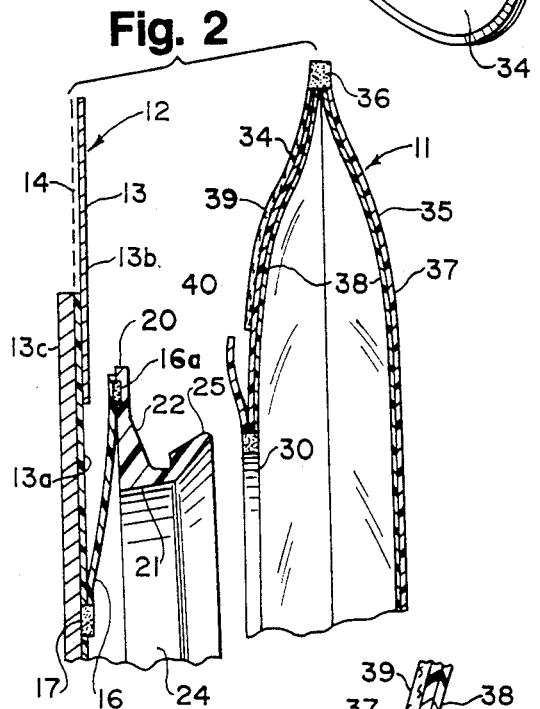
FIG. 2 is a schematic vertical sectional view of the faceplate component and the pouch component in separated condition.

As shown in FIG. 2, a thin, flexible annular web 16 extends from the panel 13 from a heat sealed connection 17. The web 16 allows a patient to insert his/her fingers behind the coupling ring so that the user may more easily attach the coupling ring to the pouch component 11 and avoid exerting axial forces against the peristomal area which may be sensitive after surgery. For further details on the use of an annular web to give the faceplate coupling ring 20 a "floating" action, reference may be had to co-owned U.S. Pat. No. 4,419,100. Although such a "floating" construction is preferred because of the advantages described, it will be understood that, if desired, the web may be omitted and coupling ring 20 may be joined directly to panel 13.

The outer margin of web 16 is heat sealed at 16a to coupling ring 20. Coupling ring 20 includes an annular base 21 having a contact face 22 and an annular collar 23 extending from the base. The base 21 defines a central opening 24 with which the collar 23 is concentric and adjacent. A bistable annular latching member 25 is joined to the collar 23 along an annular hinge line 28 shown in FIG. 3. The latching member 25 has a contact surface 25a on a side opposite from opening 24. The base portion 21, collar 23, and latching member 25 may be integrally formed of a low density polyethlene or any other suitable polymeric material having similar properties of toughness, stiffness and limited flexibility.

Figure 3:
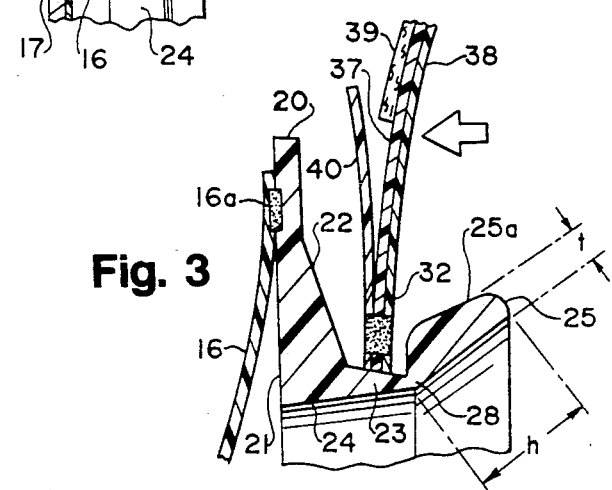
FIG. 3 is a schematic vertical sectional view of the faceplate component after the coupling ring has been inserted into the opening of the pouch component but with the coupling ring in its first untensioned stable state.

As shown in FIGS. 2 and 3, the pouch component 11 has an annular opening 30 and a peripheral area or edge portion 32 extending about that opening. The pouch component 11 is comprised of a front panel 34 and a rear panel 35 joined along their margins by heat seal 36. The front and rear panels each include an exterior layer 37 and an interior layer 38. An additional tissue layer 39 may extend over the exterior layer 34 to provide softness and promote patient comfort. Exterior layer 37 is typically made of a water soluble polymeric material which is relatively strong and tough in a dry state such as, for example, polyvinyl alcohol or polyethylene oxide. In contrast, the interior layer 38 is comprised of a water insoluble material which, because of its composition or its relative thinness, is weak and depends on the soluble layer for support and structural integrity. Upon dissolution of the soluble layer, the inner insoluble layer readily collapses or disintegrates. Suitable materials for the inner layer 38 are polyvinylidene chloride or atactic polypropylene nitrocellulose, although any of a variety of other insoluble materials may be used. The tissue layer 39 may be made of a water soluble tissue or other fabric which will easily dissolve so as to be flushable in a toilet bowl or water closet.

A thin, flexible gripping ring 40 may be connected along its inner edge portion 40a to the annular area 32 of the pouch component so that a user may grasp the ring 40 during connection to or removal from faceplate component 12. Like outer layer 37 of the pouch, the gripping ring 40 may, if desired, be formed of a tough, flexible, but water soluble polymeric material. Thus, when discarded into a flush toilet, ring 40 and outer layers 37 dissolve and layers 38 and 39 disintegrate, resulting in a pouch that is totally disposable and "flushable." It is to be understood, however, that while this invention is particularly useful with flushable pouches, the pouch 10 may be formed, if desired, of conventional non-soluble and non-disintegrating film materials.

Figure 4:
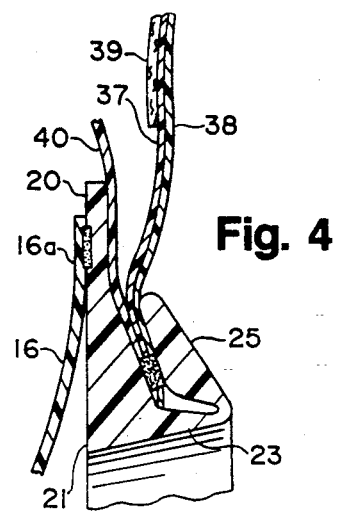
FIG. 4 is a schematic vertical sectional view illustrating the two-piece appliance with the latching member in its tensioned inverted state such that it engages the periphery of the opening in the pouch component.

A characteristic feature of the coupling ring 20 is that its latching member 25 is bistable—that is, the member is predisposed to assume in spring-like fashion either of the two stable conditions or states depicted in FIGS. 3 and 4. In its normal, untensioned state as shown in FIGS. 3 and 5, latching member 25 projects generally axially away from the base 21 and is substantially untensioned.

Figures 5, 6, 7:
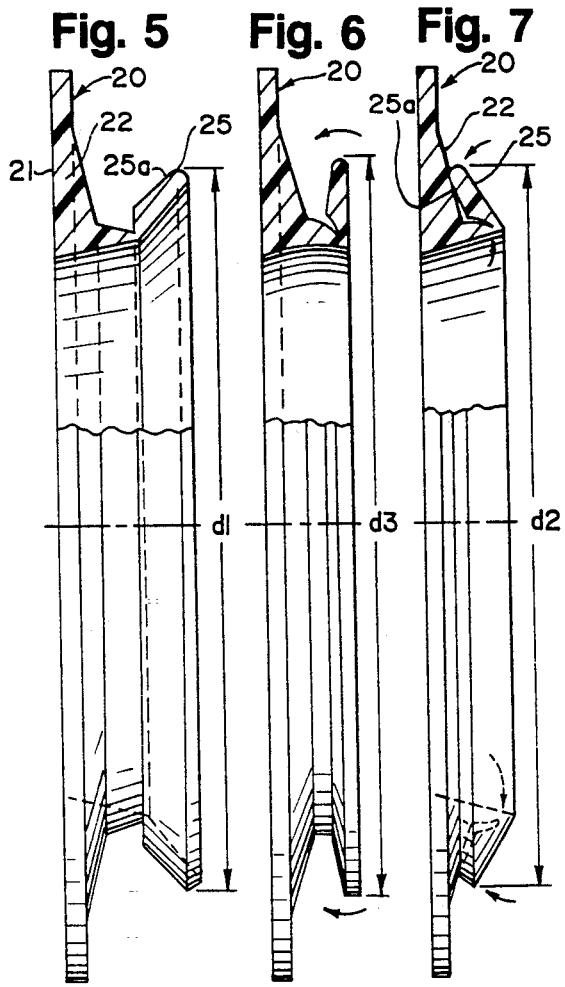
FIGS. 5–7 are schematic vertical sectional views of the coupling ring illustrating the first and second stable states of the latching member as well as an unstable intermediate or transitional state of that member.

The second stable state of the coupling ring 20 and latching member 25 is illustrated in FIGS. 4 and 7. In its second state, the latching member 25 is tensioned and extends reversely towards the base with the contact surface 25a of the latching member 25 positioned for tight engagement with the base's contact face 22 (see FIG. 7).

FIGS. 5-7 illustrate the operation of the coupling ring 20 and its bistable latching member 25. In the latching member's stable first state (FIG. 5), the free end of latching member 25 defines an opening having a diameter d1. In the latching member's stable second state (FIG. 7), the free end has a diameter d2 which is slightly greater than the diameter d1 of the first state because the latching member is under tension, its rearward pivotal movement being limited by contact face 22 of base 21. Between its two stable states or positions, the latching member has intermediate positions (FIG. 6) where it is structurally unstable and under tension. When the latching member is in an intermediate position, its diameter d3 is greater than either diameter d1 or d2 of the first and second states. The circumferential stretching of the member in such intermediate positions produces hoop stresses or tensions that urge the latching member 25 to flip in springlike fashion towards either the stable first position (FIG. 5) or the stable but tensioned second position (FIG. 7).

The length of the latching member 25 (measured between hinge 28 and the member's free end) should exceed the length of the collar 23 so that the contact surface 27 will reach and engage the contact face 22 in the latching member's second state.

In use, as shown in FIGS. 3 and 4, the coupling ring 20 is inserted into the opening 30 in the pouch 11 so that the peripheral area or annular edge portion 32 of the pouch extends about collar 23. It should be noted that the free end of the latching member 25 has a diameter substantially equal to or greater than the diameter of the opening 30 in the pouch component 11. However, even if the diameter of the free end is greater than the diameter of the opening 30, the deformable coupling ring 20 may still be easily inserted into the opening 30 by first urging an arcuate portion of the member's free end into the opening and then slightly deforming the latching member so that the remainder of the periphery may be popped into opening 30. To facilitate this connection, the user may grasp the annular gripping ring 40 to manipulate the coupling ring 20 into the opening 30.

Once the annular edge portion 32 of the pouch is fitted about collar 23, the latching member 25 can be pivoted in an axial direction towards the base 21 to clamp the annular periphery or edge portion of the pouch between contact face 22 of the base 21 and surface 25a of the latching member (FIG. 4). With latching member in its second stable state, the coupling ring 20 provides a fluid-tight latching interconnection between the pouch component 11 and the faceplate component 12. This relationship is especially advantageous because the contact surface 25a sealingly engages the water-insoluble interior layer 38 of the pouch component 11, thereby shielding and protecting the water soluble exterior layer 34 (also ring 40) from fluids flowing through the opening 30 or contained in the pouch 11.

While in the foregoing, I have disclosed an embodiment of the invention in considerable detail for purposes of illustration, it will be understood by those skilled in the art that many of these details may be varied without departing from the spirit and scope of the invention.

I claim:

1. A faceplate for a two-piece collection system comprising a thin, flexible adhesive panel for adhesive attachment to a skin surface;

a coupling ring formed of flexible, semi-rigid polymeric material;

and attachment means for joining said coupling member to said panel;

said coupling ring having an annular base defining a central opening and a contact face surrounding said opening; an annular collar extending from said base adjacent to and concentric with said opening, and a bistable annular latching member joined to said collar along an annular hinge line, said latching member providing a contact surface and being pivotal about said hinge line between a stable, substantially untensioned first state wherein said member projects generally axially away from said collar and a stable, tensioned second state wherein said member extends reversely towards said base with said contact surface of said latching member positioned for tight engagement with said base's contact face;

said latching member including a free end portion; said free end portion, when said member is in said second state, being under hoop stress and having an outside diameter greater than when said member is in said untentioned first state;

said latching member also passing through intermediate states as it is shifted between said first and second states; said free end portion having an outside diameter in said tensioned second state smaller than said outside diameter of said free end portion in said intermediate states.

2. The faceplate of claim 1 in which said coupling ring is formed integrally of said flexible, semi-rigid polymeric material.

3. The faceplate of claim 1 in which said attachment means comprises a thin, flexible annular web having an inner edge secured to said panel and a concentric outer edge secured to said base of said coupling ring.

4. A two-piece collection system comprising a pouch component and a faceplate component; said pouch component having a wall defining a stoma receiving opening; said faceplate component comprising a thin, flexible adhesive panel for adhesive attachment to a skin surface, a coupling ring formed of flexible, semi-rigid polymeric material, and attachment means for joining said coupling ring to said panel; said coupling ring having a base defining a central opening and a contact face surrounding said opening; an annular collar extending from said base adjacent to and concentric with said opening, and a bistable annular latching member joined to said collar along an annular hinge line, said latching member providing a contact surface and being pivotal about said hinge line between a stable, substantially untensioned first state wherein said latching member projects generally axially away from said collar and a stable tensioned second state wherein said latching member extends reversely towards said base with said contact surface of said latching member releasably engaging a portion of said wall of said pouch component surrounding said stoma opening and clamping said wall portion against said contact face of said base, said stoma receiving opening of the pouch component having a diameter smaller than a maximum outside diameter of the latching member when the latching member is in its second stable state.

5. The two-piece ostomy appliance in claim 4 in which said coupling ring is integrally formed of said flexible, semi-rigid polymeric material.

6. The two-piece ostomy appliance of claim 4 in which said latching member includes a free end portion; said free end portion, when said latching member is in its second state, being under hoop stress and having an outside diameter greater than when said latching member is in said untensioned first state.

7. The two-piece ostomy appliance of claim 6 in which said latching member passes through intermediate states as it is shifted between said first and second states, said free end portion having an outside diameter in said tensioned state smaller than the outside diameter of said free end portion in said intermediate states.

8. The two-piece ostomy appliance of claim 4 in which said attachment means comprises a thin, flexible annular web having an inner edge secured to said panel and a concentric outer edge secured to said base of said coupling ring.

9. The two-piece ostomy appliance of claim 4 in which said pouch component includes a flexible annular gripping ring having an inner edge portion externally secured to a peripheral area of said wall of said pouch component about said stoma receiving opening.

10. The two-piece ostomy appliance of claim 4 in which said wall of said pouch component is comprised of a relatively thin and weak water-insoluble interior layer and a relatively strong but water-soluble exterior layer.

11. The two-piece ostomy appliance of claim 10 in which said water-soluble exterior layer has an exposed edge at said stoma receiving opening; said base, collar, and latching member of said coupling ring shielding said edge from contact with fluids passing through said latching member, collar, and base when said components are coupled together.

12. The two-piece ostomy appliance of claim 9 in which said gripping ring is formed of a water soluble polymeric material.

* * * * *